United States Patent
Cai

(10) Patent No.: US 12,150,810 B2
(45) Date of Patent: Nov. 26, 2024

(54) INTRAVASCULAR IMAGING SYSTEM WITH AUTOMATED CALCIUM ANALYSIS AND TREATMENT GUIDANCE

(71) Applicant: Boston Scientific Scimed, Inc., Maple Grove, MN (US)

(72) Inventor: Anming He Cai, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 65 days.

(21) Appl. No.: 17/889,753

(22) Filed: Aug. 17, 2022

(65) Prior Publication Data
US 2023/0056254 A1 Feb. 23, 2023

Related U.S. Application Data

(60) Provisional application No. 63/233,875, filed on Aug. 17, 2021.

(51) Int. Cl.
*A61B 5/05* (2021.01)
*A61B 8/00* (2006.01)
(Continued)

(52) U.S. Cl.
CPC .............. *A61B 8/12* (2013.01); *A61B 8/0891* (2013.01); *A61B 8/463* (2013.01); *A61B 8/5215* (2013.01);
(Continued)

(58) Field of Classification Search
CPC ......... A61B 8/12; A61B 8/0891; A61B 8/463; A61B 8/5215; A61B 2034/102
See application file for complete search history.

(56) References Cited

U.S. PATENT DOCUMENTS

| 6,109,270 A | 8/2000 | Mah et al. |
| 6,945,938 B2 | 9/2005 | Grunwald |

(Continued)

FOREIGN PATENT DOCUMENTS

| CN | 107909585 A | 4/2018 |
| CN | 110070529 A | 7/2019 |

(Continued)

OTHER PUBLICATIONS

International Search Report and Written Opinion dated Dec. 4, 2020 for International Application No. PCT/US2020/052517.
(Continued)

*Primary Examiner* — Joel F Brutus
(74) *Attorney, Agent, or Firm* — Seager, Tufte & Wickhem, LLP

(57) ABSTRACT

Intravascular imaging systems and methods for making and using intravascular imaging devices are disclosed. An example intravascular imaging device may comprise a catheter including an imaging device. A processor may be coupled to the catheter. The processor may be configured to process image data received from the imaging device. The processor may be configured to generate a calcium map. The calcium map may include an indicator of calcium depth to a vessel lumen surface, calcium distance to a center of the catheter, or both. A display unit may be coupled to the processor. The display unit may be configured to show a display including the calcium map.

16 Claims, 14 Drawing Sheets

(51) Int. Cl.
*A61B 8/08* (2006.01)
*A61B 8/12* (2006.01)
*A61B 17/3207* (2006.01)
*A61B 34/10* (2016.01)

(52) U.S. Cl.
CPC .......... *A61B 17/3207* (2013.01); *A61B 34/10* (2016.02); *A61B 2034/102* (2016.02)

(56) References Cited

U.S. PATENT DOCUMENTS

| | | | |
|---|---|---|---|
| 7,133,546 B2 | 11/2006 | Dehmeshki et al. |
| 7,246,959 B2 | 7/2007 | Nakatani |
| 7,306,561 B2 | 12/2007 | Sathyanarayana |
| 7,460,716 B2 | 12/2008 | Sathyanarayana |
| 7,545,965 B2 | 6/2009 | Suzuki et al. |
| 8,290,228 B2 | 10/2012 | Cohen et al. |
| 8,313,437 B1 | 11/2012 | Suri |
| 8,463,007 B2 | 6/2013 | Steinberg et al. |
| 8,485,975 B2 | 7/2013 | Sur |
| 8,532,360 B2 | 9/2013 | Suri |
| 8,542,900 B2 | 9/2013 | Tolkowsky et al. |
| 8,639,008 B2 | 1/2014 | Suri |
| 8,670,603 B2 | 3/2014 | Tolkowsky et al. |
| 8,693,756 B2 | 4/2014 | Tolkowsky et al. |
| 8,700,130 B2 | 4/2014 | Iddan et al. |
| 8,708,914 B2 | 4/2014 | Suri |
| 8,781,193 B2 | 7/2014 | Steinberg et al. |
| 8,805,043 B1 | 8/2014 | Suri |
| 8,855,744 B2 | 10/2014 | Tolkowsky et al. |
| 9,008,367 B2 | 4/2015 | Tolkowsky et al. |
| 9,008,754 B2 | 4/2015 | Steinberg et al. |
| 9,014,453 B2 | 4/2015 | Steinberg et al. |
| 9,144,394 B2 | 5/2015 | Cohen et al. |
| 9,095,313 B2 | 8/2015 | Tolkowsky et al. |
| 9,101,286 B2 | 8/2015 | Tolkowsky et al. |
| 9,216,065 B2 | 12/2015 | Cohen et al. |
| 9,305,334 B2 | 4/2016 | Barzelay et al. |
| 9,308,052 B2 | 4/2016 | Tolkowsky |
| 9,375,164 B2 | 6/2016 | Tolkowsky et al. |
| 9,629,571 B2 | 4/2017 | Tolkowsky et al. |
| 9,679,374 B2 | 6/2017 | Choi et al. |
| 9,717,415 B2 | 8/2017 | Cohen et al. |
| 9,805,463 B2 | 10/2017 | Choi et al. |
| 9,855,384 B2 | 1/2018 | Cohen et al. |
| 9,888,969 B2 | 2/2018 | Cohen et al. |
| 9,924,927 B2 | 3/2018 | Shin et al. |
| 9,968,256 B2 | 5/2018 | Tolkowsky et al. |
| 9,974,509 B2 | 5/2018 | Steinberg et al. |
| 10,152,788 B2 | 12/2018 | Klaiman et al. |
| 10,176,408 B2 | 1/2019 | Paik et al. |
| 10,176,575 B2 | 1/2019 | Isgum et al. |
| 10,226,178 B2 | 3/2019 | Cohen et al. |
| 10,226,235 B2 | 3/2019 | Deng et al. |
| 10,275,881 B2 | 4/2019 | Cardinal et al. |
| 10,292,676 B2 | 5/2019 | Rajguru et al. |
| 10,307,061 B2 | 6/2019 | Cohen et al. |
| 10,362,962 B2 | 7/2019 | Cohen et al. |
| 10,413,317 B2 | 9/2019 | Whiseant |
| 10,499,814 B2 | 12/2019 | Steinberg et al. |
| 10,561,401 B2 | 2/2020 | Cai et al. |
| 10,568,586 B2 | 2/2020 | Begin et al. |
| 10,671,896 B2 | 6/2020 | Reicher et al. |
| 10,699,407 B2 | 6/2020 | Isgum et al. |
| 10,716,528 B2 | 7/2020 | Tolkowsky et al. |
| 10,748,277 B2 | 8/2020 | Zhou et al. |
| 10,748,289 B2 | 8/2020 | Tolkowsky et al. |
| 10,762,637 B2 | 9/2020 | Gulsun et al. |
| 10,803,583 B2 | 10/2020 | Wang et al. |
| 10,803,994 B2 | 10/2020 | Lavi et al. |
| 10,806,516 B2 | 10/2020 | Germain et al. |
| 10,888,234 B2 | 1/2021 | Sharma et al. |
| 2006/0100522 A1 | 5/2006 | Yuan et al. |
| 2006/0106320 A1 | 5/2006 | Barbato |
| 2006/0173350 A1 | 8/2006 | Yuan et al. |
| 2006/0253028 A1 | 11/2006 | Lam et al. |
| 2007/0016054 A1 | 1/2007 | Cao et al. |
| 2007/0038111 A1 | 2/2007 | Rehrig et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2010/0157041 A1 | 6/2010 | Klaiman et al. |
| 2010/0228076 A1 | 9/2010 | Blank et al. |
| 2011/0257505 A1 | 10/2011 | Suri |
| 2011/0257545 A1 | 10/2011 | Suri |
| 2012/0029339 A1 | 2/2012 | Cohen et al. |
| 2014/0094691 A1 | 4/2014 | Steinberg et al. |
| 2014/0107479 A1 | 4/2014 | Klaiman et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |
| 2014/0270436 A1* | 9/2014 | Dascal ................. A61B 5/0073 382/130 |
| 2015/0073279 A1 | 3/2015 | Cai et al. |
| 2015/0282890 A1 | 10/2015 | Cohen et al. |
| 2015/0283319 A1 | 10/2015 | Tolkowsky et al. |
| 2017/0032523 A1 | 2/2017 | Klaiman et al. |
| 2017/0076014 A1 | 3/2017 | Bressloff |
| 2017/0367768 A1 | 12/2017 | Zarkh |
| 2017/0367769 A1 | 12/2017 | Zarkh |
| 2018/0103912 A1 | 4/2018 | Canfield et al. |
| 2018/0129900 A1 | 5/2018 | Kiraly et al. |
| 2019/0150896 A1 | 5/2019 | Deng et al. |
| 2019/0159737 A1 | 5/2019 | Buckler et al. |
| 2019/0172197 A1 | 6/2019 | Buckler et al. |
| 2019/0180153 A1 | 6/2019 | Buckler et al. |
| 2019/0180438 A1 | 6/2019 | Buckler et al. |
| 2019/0205606 A1 | 7/2019 | Zhou et al. |
| 2019/0213761 A1 | 7/2019 | Rosen et al. |
| 2019/0244347 A1 | 8/2019 | Buckler et al. |
| 2020/0085386 A1 | 3/2020 | Klaiman et al. |
| 2020/0121291 A1 | 4/2020 | Cai et al. |
| 2020/0129147 A1 | 4/2020 | Nair et al. |
| 2020/0205750 A1 | 7/2020 | Begin et al. |
| 2020/0226422 A1* | 7/2020 | Li ........................... G06N 3/04 |
| 2020/0257919 A1 | 8/2020 | Karmon et al. |
| 2024/0057870 A1 | 2/2024 | Gopinath et al. |

FOREIGN PATENT DOCUMENTS

| | | |
|---|---|---|
| KR | 20170113251 A | 10/2017 |
| WO | 2017130927 A1 | 8/2017 |
| WO | 2020190976 A3 | 9/2020 |
| WO | 2021062006 A1 | 4/2021 |

OTHER PUBLICATIONS

U.S. Appl. No. 17/960,812, filed Oct. 5, 2022.
International Search Report and Written Opinion dated Nov. 30, 2022 for International Application No. PCT/US2022/040584.

* cited by examiner

INTRAVASCULAR IMAGING SYSTEM WITH AUTOMATED CALCIUM ANALYSIS AND TREATMENT GUIDANCE

CROSS REFERENCE TO RELATED APPLICATIONS

This application claims the benefit of priority under 35 U.S.C. § 119 of U.S. Provisional Application No. 63/233,875, filed Aug. 17, 2021, the entire disclosure of which is hereby incorporated by reference.

TECHNICAL FIELD

The present disclosure pertains to medical imaging. More particularly, the present disclosure pertains to intravascular imaging.

BACKGROUND

A wide variety of medical devices have been developed for medical use, for example, intravascular use. Some of these devices include intravascular imaging devices. In addition, methods for intravascular imaging have been developed. Of these devices and methods, each has certain advantages and disadvantages. There is an ongoing need to provide alternative devices as well as alternative methods.

BRIEF SUMMARY

This disclosure provides design, material, manufacturing method, and use alternatives for medical devices. An intravascular imaging system is disclosed. The intravascular imaging system comprises: a catheter including an imaging device; a processor coupled to the catheter, the processor configured to process image data received from the imaging device; wherein the processor is configured to generate a calcium map; wherein the calcium map includes an indicator of calcium depth to a vessel lumen surface, calcium distance to a center of the catheter, or both; and a display unit coupled to the processor, the display unit being configured to show a display including the calcium map.

Alternatively or additionally to any of the embodiments above, the horizontal axis in the calcium map represents the catheter pullback direction.

Alternatively or additionally to any of the embodiments above, the vertical axis in the calcium map represents the catheter rotation angle.

Alternatively or additionally to any of the embodiments above, the calcium map includes a topographic depiction of calcium depth to the vessel lumen surface.

Alternatively or additionally to any of the embodiments above, the calcium map includes a topographic depiction of calcium distance to the center of the catheter.

Alternatively or additionally to any of the embodiments above, the calcium map includes a grayscale depiction of calcium depth to the vessel lumen surface.

Alternatively or additionally to any of the embodiments above, the calcium map includes a grayscale depiction of calcium distance to the center of the catheter.

Alternatively or additionally to any of the embodiments above, the display includes a transverse cross-sectional depiction of a blood vessel.

Alternatively or additionally to any of the embodiments above, the transverse cross-sectional depiction of the blood vessel includes one or more treatment device representations overlaid thereon.

Alternatively or additionally to any of the embodiments above, the one or more treatment device representations includes one or more depictions of a rotational atherectomy device size.

Alternatively or additionally to any of the embodiments above, the display includes a plurality of panels corresponding to different time periods during an intervention.

Alternatively or additionally to any of the embodiments above, the plurality of panels includes a pre-treatment panel, a lesion prep panel, and a post-treatment panel.

Alternatively or additionally to any of the embodiments above, the imaging device includes an intravascular ultrasound device.

Alternatively or additionally to any of the embodiments above, the imaging device includes an optical coherence tomography device.

An intravascular imaging system is disclosed. The intravascular imaging system comprises: a catheter system including an intravascular imaging device; a processor coupled to the catheter system, the processor configured to process image data received from the intravascular imaging device; wherein the processor is configured to generate a calcium map that graphically depicts an indicator of calcium depth to a vessel lumen surface, calcium distance to a center of the catheter system, or both; and a display unit coupled to the processor, the display unit being configured to show a display including the calcium map.

Alternatively or additionally to any of the embodiments above, the calcium map includes a topographic depiction of calcium depth to the vessel lumen surface.

Alternatively or additionally to any of the embodiments above, the calcium map includes a topographic depiction of calcium distance to the center of the catheter system.

Alternatively or additionally to any of the embodiments above, the display includes a transverse cross-sectional depiction of a blood vessel.

Alternatively or additionally to any of the embodiments above, the transverse cross-sectional depiction of the blood vessel includes one or more treatment device representations overlaid thereon.

Alternatively or additionally to any of the embodiments above, the one or more treatment device representations includes one or more depictions of a rotational atherectomy device size.

Alternatively or additionally to any of the embodiments above, the display includes a plurality of panels corresponding to different time periods during an intervention including a pre-treatment panel, a lesion prep panel, and a post-treatment panel.

An intravascular imaging system is disclosed. The intravascular imaging system comprises: a catheter system including an intravascular ultrasound imaging device; a processor computed to the catheter system, the processor configured to process image data received from the intravascular ultrasound imaging device; wherein the processor is configured to use artificial intelligence to generate a calcium map that graphically depicts an indicator of calcium depth to a vessel lumen surface, calcium distance to a center of the catheter system, or both; and a display unit coupled to the processor, the display unit being configured to show a display including the calcium map.

An intravascular imaging system is disclosed. The intravascular imaging system comprises: a catheter including an imaging device; a processor coupled to the catheter, the processor configured to process image data received from the imaging device; wherein the processor is configured to generate a 3-dimensional video of a blood vessel.

Alternatively or additionally to any of the embodiments above, the 3-dimensional video is obtained through a 3-dimensional lumen surface or volume rendering.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
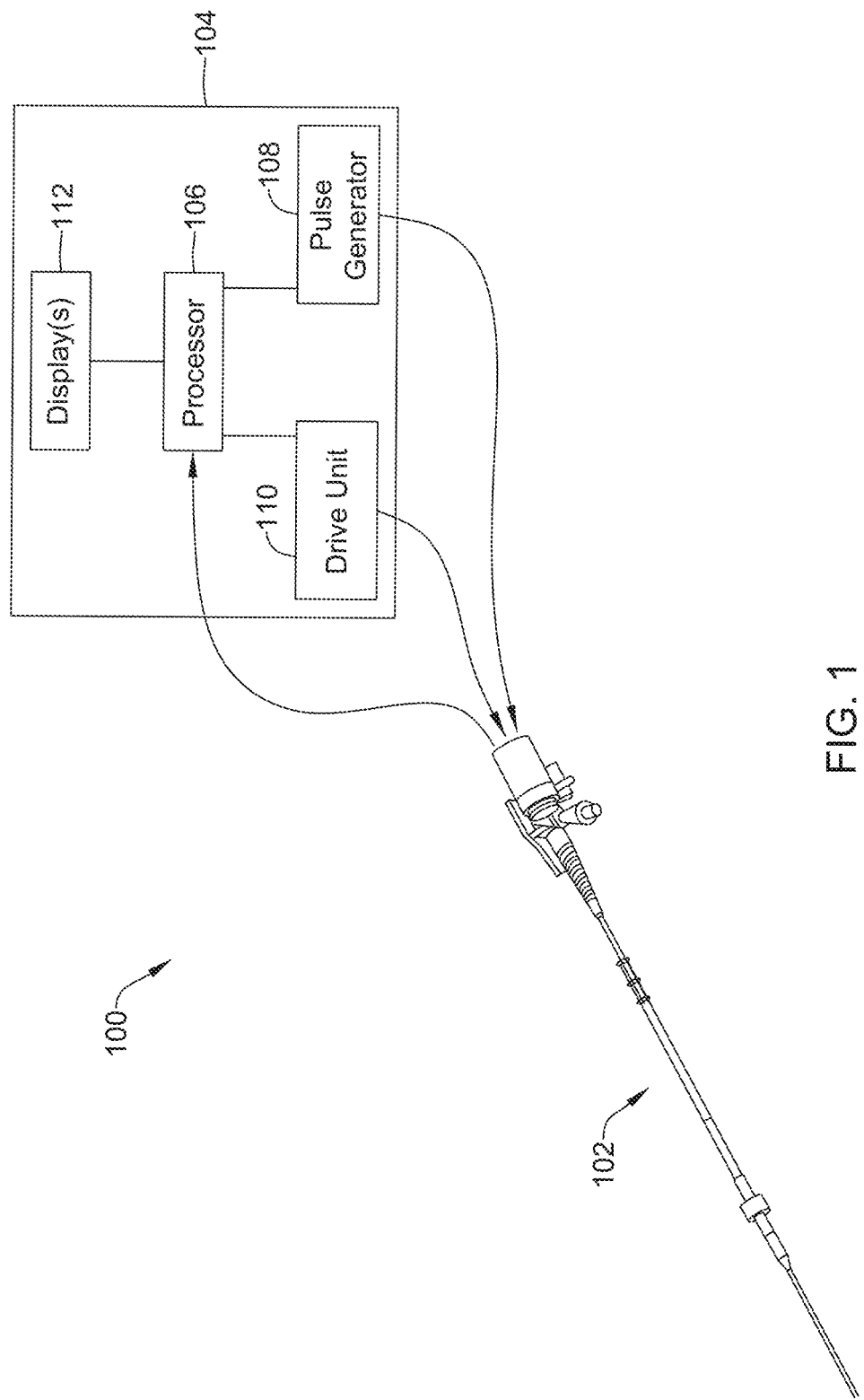
FIG. 1 schematically depicts an example intravascular imaging system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Intravascular imaging devices insertable into patients have proven diagnostic capabilities for a variety of diseases and disorders. For example, intravascular ultrasound ("IVUS") imaging systems and or optical coherence tomography ("OCT") imaging systems may be used as an imaging modality for diagnosing blocked blood vessels and providing information to aid medical practitioners in selecting and placing stents and other devices to restore or increase blood flow. IVUS/OCT imaging systems may also be used to diagnose atheromatous plaque build-up at particular locations within blood vessels. IVUS/OCT imaging systems may also be used to determine the existence of an intravascular obstruction or stenosis, as well as the nature and degree of the obstruction or stenosis. IVUS/OCT imaging systems may also be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS/OCT imaging systems may also be used to monitor or assess ongoing intravascular treatments, such as angiography and stent placement in real (or almost real) time. Moreover, IVUS/OCT imaging systems may be used to monitor one or more heart chambers.

FIG. 1 illustrates schematically an example intravascular imaging system 100. In this example, the intravascular imaging system 100 takes the form of an IVUS imaging system. However, other imaging systems are contemplated including optical coherence tomography imaging systems. The IVUS imaging system 100 includes a catheter 102 that is coupleable to a processing unit or control module 104. The control module 104 may include, for example, a processor 106, a pulse generator 108, a drive unit 110, and one or more displays or display units 112. In some instances, the pulse generator 108 forms electric pulses that may be input to one or more transducers (312 in FIG. 3) disposed in the catheter 102.

For the purposes of this disclosure, the term "display" may either refer to an electronic device (e.g., such as a monitor, etc.) used for the visual representation of data or to the visual representation of data itself. In other words, the term "display" may refer to a hardware device for displaying data or the term "display" may refer to the data displayed on the hardware device. In some cases, it may be helpful to use the phrase "display unit" when referring to the hardware component and the term "display" when referring to the visual/data component shown on the display unit. However, such terminology need not be strictly adhered to in this disclosure or in the art in general. One of skill in the art would be able to discern when the term "display" is referring to a hardware component and when the term "display" is referring to the visual/data component.

In some instances, mechanical energy from the drive unit 110 may be used to drive an imaging core (306 in FIG. 3) disposed in the catheter 102. In some instances, electric signals transmitted from the one or more transducers (312 in FIG. 3) may be input to the processor 106 for processing. In some instances, the processed electric signals from the one or more transducers (312 in FIG. 3) can be displayed as one or more images on the one or more display units 112. For example, a scan converter can be used to map scan line samples (e.g., radial scan line samples, or the like) to a two-dimensional Cartesian grid to display the one or more images on the one or more display units 112.

In some instances, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more display units 112.

Figure 2:
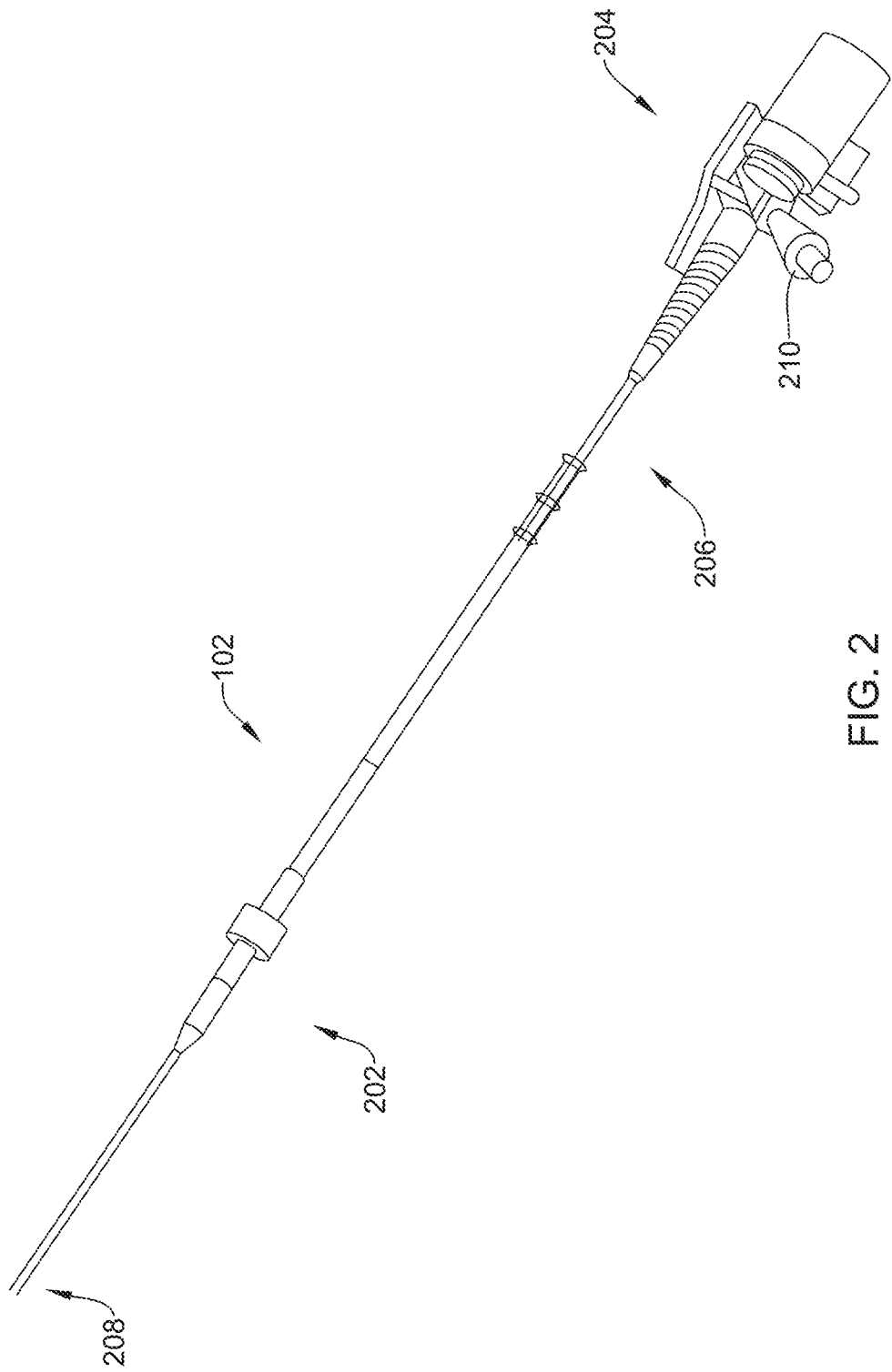
FIG. 2 is a perspective view of an example intravascular imaging catheter system.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some instances, the elongated member 202 and the hub 204 are formed as a unitary body. In other instances, the elongated member 202 and the catheter hub 204 are formed separately and subsequently assembled together.

Figure 3:
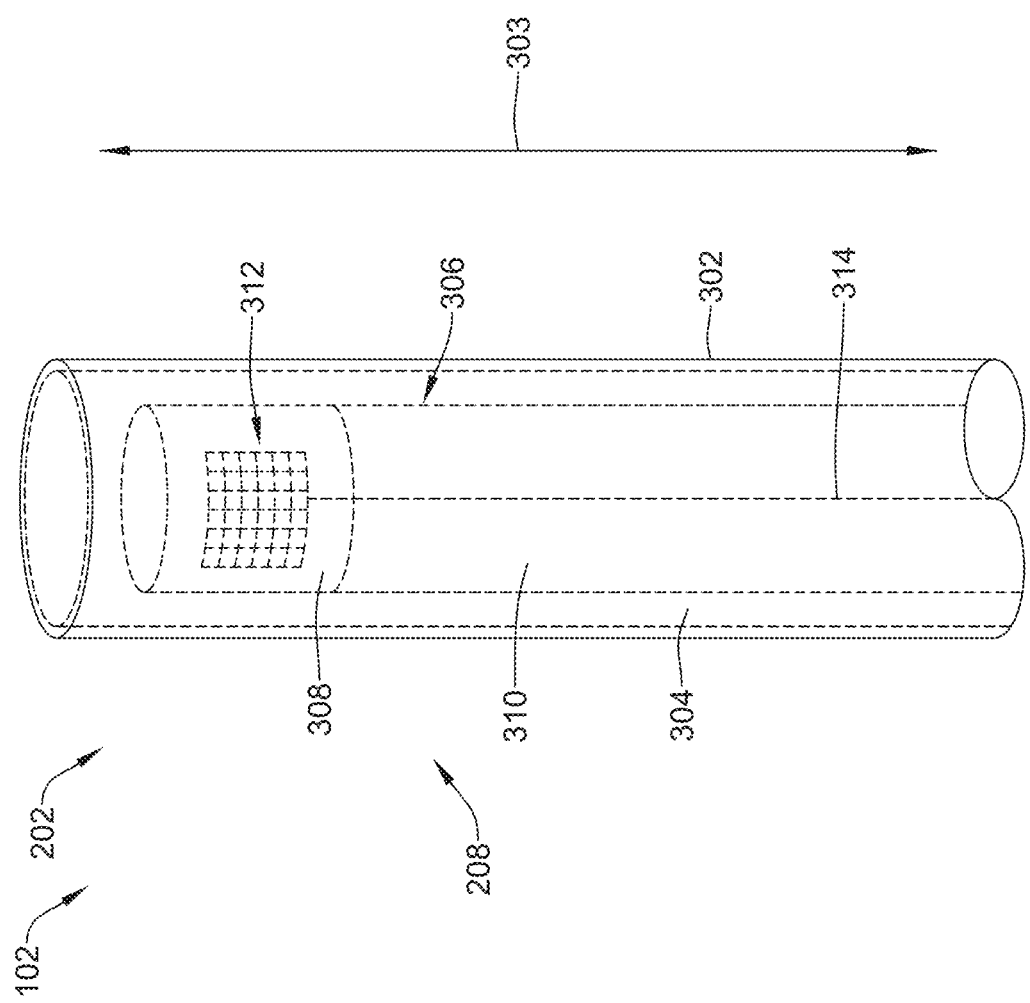
FIG. 3 is a side view of a portion of an example intravascular imaging catheter system.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or using a computer-controlled drive mechanism. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In some instances, for example as shown in FIG. 3, an array of transducers 312 are mounted to the imaging device 308. Alternatively, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidene fluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 is rotated about the longitudinal axis 303 of the catheter 102. As the imaging core 306 rotates, the one or more transducers 312 emit acoustic signals in different radial directions (e.g., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In some instances, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more display units 112. The at least one of the imaging core 306 can be either manually rotated or rotated using a computer-controlled mechanism.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (e.g., pulled back) along the longitudinal length of the catheter 102. The catheter 102 can include at least one telescoping section that can be retracted during pullback of the one or more transducers 312. In some instances, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

A stepper motor may, optionally, be used to pull back the imaging core 306. The stepper motor can pull back the imaging core 306 a short distance and stop long enough for the one or more transducers 306 to capture an image or series of images before pulling back the imaging core 306 another short distance and again capturing another image or series of images, and so on.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In some instances, the IVUS imaging system 100 operates within a frequency range of 5 MHz to 100 MHz.

One or more conductors 314 can electrically couple the transducers 312 to the control module 104 (see, for example, FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

An image or image frame ("frame") can be generated each time one or more acoustic signals are output to surrounding tissue and one or more corresponding echo signals are received by the imager 308 and transmitted to the processor 106. Alternatively, an image or image frame can be a composite of scan lines from a full or partial rotation of the imaging core or device. A plurality (e.g., a sequence) of frames may be acquired over time during any type of movement of the imaging device 308. For example, the frames can be acquired during rotation and pullback of the imaging device 308 along the target imaging location. It will be understood that frames may be acquired both with or without rotation and with or without pullback of the imaging device 308. Moreover, it will be understood that frames may be acquired using other types of movement procedures in addition to, or in lieu of, at least one of rotation or pullback of the imaging device 308.

In some instances, when pullback is performed, the pullback may be at a constant rate, thus providing a tool for potential applications able to compute longitudinal vessel/plaque measurements. In some instances, the imaging device 308 is pulled back at a constant rate of at least 0.3 mm/s. In some instances, the imaging device 308 is pulled back at a constant rate of at least 0.4 mm/s. In some instances, the imaging device 308 is pulled back at a constant rate of at least 0.5 mm/s. In some instances, the imaging device 308 is pulled back at a constant rate of at least 0.6 mm/s. In some instances, the imaging device 308 is pulled back at a constant rate of at least 0.7 mm/s. In some instances the imaging device 308 is pulled back at a constant rate of at least 0.8 mm/s.

In some instances, the one or more acoustic signals are output to surrounding tissue at constant intervals of time. In some instances, the one or more corresponding echo signals are received by the imager 308 and transmitted to the processor 106 at constant intervals of time. In some instances, the resulting frames are generated at constant intervals of time.

At least some conventional IVUS imaging systems display only a single (e.g., cross-sectional, longitudinal, or the like) image during, or after, an IVUS procedure, such as a pull-back procedure. It may, however, be useful to concurrently display, in real-time during the IVUS procedure (e.g., a pull-back procedure), at least two images, such as the most recently processed image and a previously-obtained image that has some particular or selected image characteristic (e.g., maximum or minimum lumen area or diameter).

Some diagnostic and/or therapeutic interventions may include the analysis of images generated by the IVUS imaging system. This analysis, however, may require a substantial amount of training/experience in order to efficiently interpret the images. Further, due to the frequent presence of speckles on IVUS images, automated analysis and/or evaluation may also be challenging. Disclosed herein are methods for processing and/or analyzing images such as images generated with/by an IVUS imaging system. Such methods may utilize machine learning, artificial intelligence, deep neural networks, and/or the like to improve the processing and/or analysis of images generated with/by an IVUS imaging system.

Figure 4:
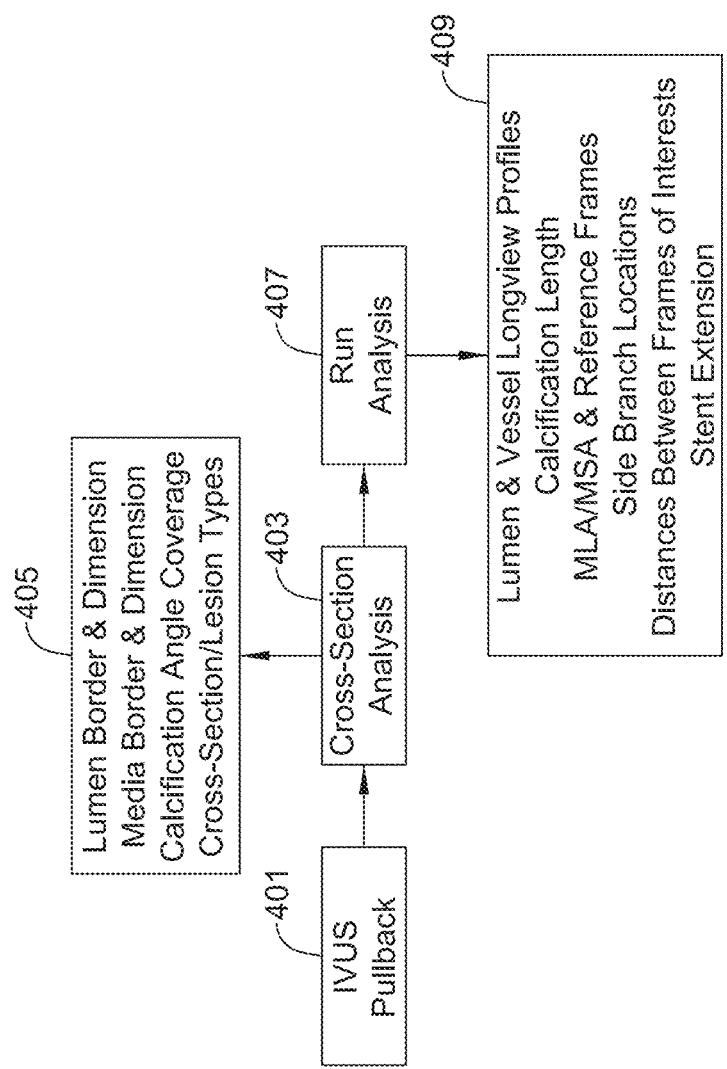
FIG. 4 is a flow chart illustrating an example method for processing images.

FIG. 4 is a flow chart illustrating an overview or framework of an example process. The process may include the generation and/or collection of images of a blood vessel (e.g., IVUS images, cross-sectional images, etc. generated via an IVUS pullback procedure) at box 401. The generated/collected images may be subjected to a cross-sectional analysis at box 403. The cross-sectional analysis may include processing and/or segmentation of the images using deep learning networks (e.g., deep neural networks such as the U-Net deep neural network) to obtain image segmentation for quantitative analysis and image classification for automated identification of lesion type, stent detection, and the like. For example, output from cross-sectional analysis, marked at box 405, may include identification of the lumen border, identification of the lumen dimensions, identification of the media border (e.g., identification of a media border for media within the blood vessel), identification of the media dimensions, identification of the calcification angle/arc, identification of the calcification coverage, identification of the lesion types, and/or the like. In addition to identifying such border/dimension, the output may be displayed on a display unit in a suitable format (e.g., graphically, numerically, as a real or schematic image, with words or symbols, etc.). In some instances, multiple images of an IVUS pullback or "run" may be analyzed at box 407. The output of this run analysis, marked at box 409, may include a lumen profile (e.g., including, for example, a longitudinal cross-section or "long view"), a vessel profile (e.g., including, for example, a longitudinal cross-section or "long view"), a representation (e.g., visualization or image, numerical visualization, graphical visualization, and/or the like) of the calcification length, the depiction/display of reference frames (e.g., such as the minimal lumen area or "MLA", the minimal stent area or "MSA", or the like), a representation (e.g., visualization or image, numerical visualization, graphical visualization, and/or the like) of side branch location, a representation (e.g., visualization or image, numerical visualization, graphical visualization, and/or the like) of the distance between two frames of interest, a representation (e.g., visualization or image, numerical visualization, graphical visualization, and/or the like) of stent extension, combinations thereof, and/or the like. This may also include analyzing the images with a deep neural network (e.g., such as UNet deep neural network) and/or machine learning and/or artificial intelligence.

Figure 5:
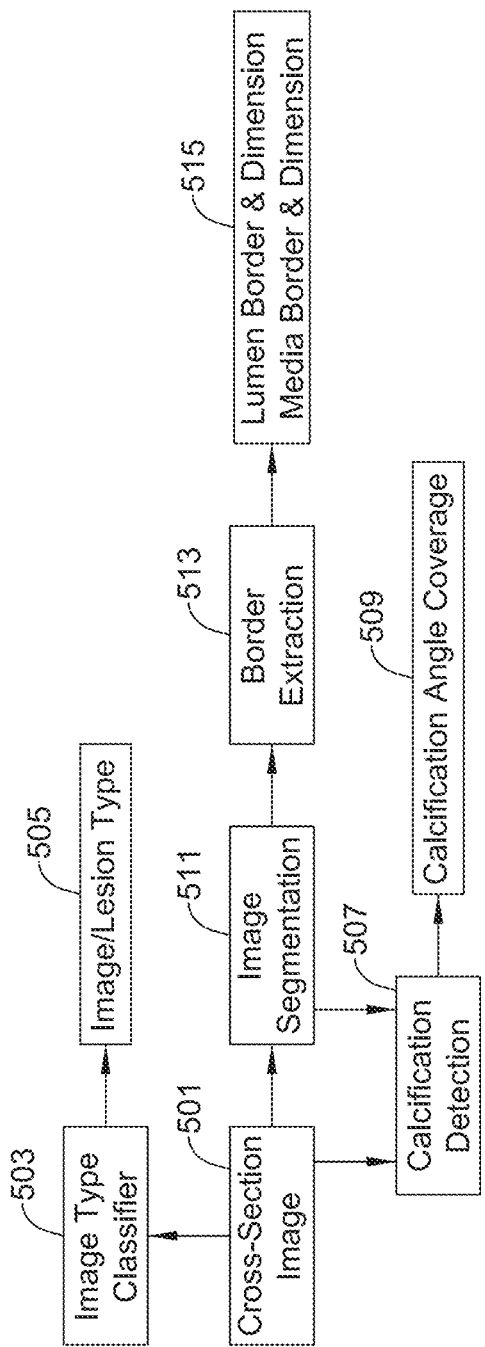
FIG. 5 is a flow chart illustrating an example method for processing images.

FIG. 5 is a flow chart depicting an example process by which an image (e.g., IVUS images, cross-sectional images, etc. generated via an IVUS pullback procedure) may be processed/segmented. For example, an example cross-sectional image (e.g., at box 501) or a group/collection of images may undergo image classification (e.g., at box 503), for example to identify the type of lesion (e.g., at box 505). In some instances, the output may be displayed on a display unit in a suitable format (e.g., graphically, numerically, as a real or schematic image, with words or symbols, etc.). In some instances, an image (e.g., at box 501) may undergo calcification detection (e.g., at box 507) to identify the calcium/calcification angle or arc coverage (e.g., at box 509).

In some instances, an image (e.g., at box 501) may undergo image segmentation (e.g., at box 511). This may include the extraction of borders (e.g., at box 513) in order to identify the lumen border, identify the dimensions of the lumen, identify the media border, identify the dimensions of the media, and/or the like (e.g., at box 515). An image of the blood vessel 517 may undergo image segmentation. This may include analyzing the image with a deep neural network (e.g., such as the U-Net deep neural network and/or other networks trained to identify a lumen border, a media border, or both) and/or machine learning and/or artificial intelligence. This may result in a visualization 519 where the lumen border 521 and the media border 523 are identified.

Interpreting calcium-related metrics/properties associated with intravascular calcification may require extensive experience by a skilled clinician. There is an ongoing need to provide a user-friendly display of various calcium-related metrics/properties that allow clinicians of a variety of differing skill levels to readily assess a patient prior to, during, and/or after an intervention. Disclosed herein are imaging devices and/or systems as well as methods for assessing blood vessels. Some of these devices/methods may be used to analyze calcification of blood vessels, for example in order to help guide treatment. This may include software and/or processing algorithms that take advantage of artificial intelligence, machine learning, neural networks, and/or the like as disclosed herein to analyze calcification of blood vessels.

Figure 6:
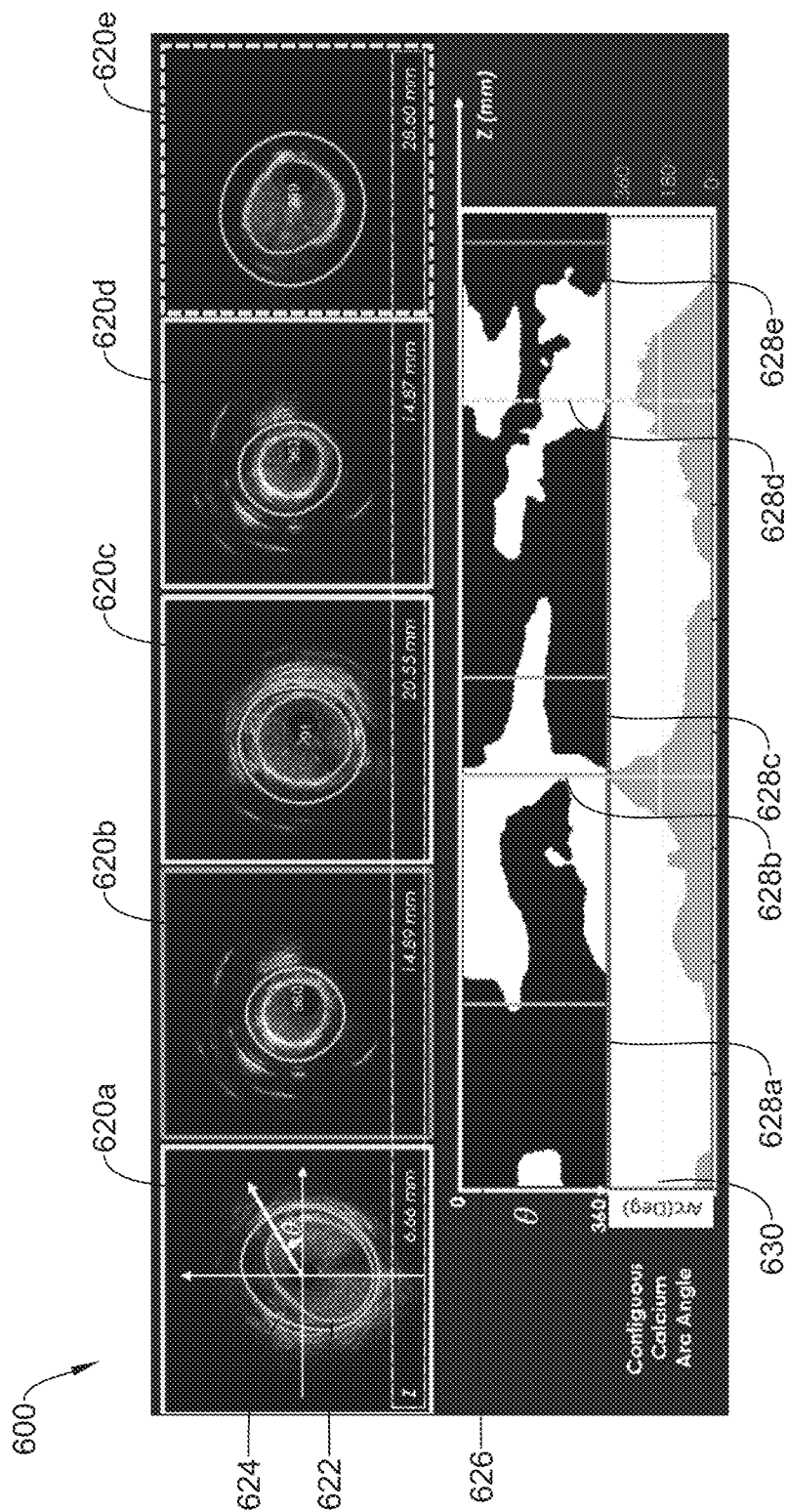
FIG. 6 illustrates a display for intravascular imaging data.

FIG. 6 illustrates a display 600 (e.g., where the display 600 refers to a visual/data component that may be displayed on a hardware component such as a display/display unit). The display 600 may include one or more transverse cross-sectional images of a blood vessel such as images 620a, 620b, 620c, 620d, 620e. In this example, the cross-sectional images 620a, 620b, 620c, 620d, 620e are IVUS images of the blood vessel. It can be appreciated that other displays are contemplated that utilize different images such as OCT images. The cross-sectional images 620a, 620b, 620c, 620d, 620e may be user selected or the processor (e.g., the processor 106) may automatically select images of desired/example locations (e.g., such as where the lumen area is minimal, reference points adjacent to the minimum lumen area, etc.). In some instances, the cross-sectional images 620a, 620b, 620c, 620d, 620e (e.g., the data used to generate the images 620a, 620b, 620c, 620d, 620e) may be processed (e.g., using the processor 106) so that additional features may be marked thereon. For example, an indication of the lumen surface 622 and/or an indication of the vessel surface 624 may be marked on the images 620a, 620b, 620c, 620d, 620e.

The display 600 may also include a calcium map 626. The calcium map 626 may be shown as a longitudinal representation of the vessel, depicted in a flattened or planar view. In other words, the longitudinal representation may be akin to taking a generally cylindrical or tubular structure (e.g., the blood vessel) and making a longitudinal slice in the tubular structure so that the tubular structure can be laid flat. In the calcium map, the horizontal axis may represent the catheter pullback direction and the vertical axis may represent the catheter (e.g., scan line) rotation angle. The calcium map 626 may include one or more reference markings/indicators such as reference markings 628a, 628b, 628c, 628d, 628e. In some instances, the reference markings 628a, 628b, 628c, 628d, 628e may include manipulatable by a user (e.g., using a scrubber or other user-manipulatable feature that allows the reference markings 628a, 628b, 628c, 628d, 628e to be moved in a side-to-side manner). For example, in FIG. 6, reference marking 628d is shown with a dashed line, indicating that this reference marking is selected by a user. In this example, image 620e is shown with a dashed perimeter, indicating that the cross-sectional image 620e corresponds to the selected reference marking 628d. The selected reference marking 628d can be shifted by a user (e.g., by moving a scrubber that appears on the display 600 when an input device is disposed adjacent to the reference marking 628d). When the reference marking 628d is shifted, the corresponding image 620e may update to show a new/updated image corresponding to the new location along the calcium map 626 that the reference marking 628d is moved to. It can be appreciated that any of the reference markings 628a, 628b, 628c, 628d, 628e can be similarly manipulated in order to allow a user to see an updated cross-sectional image at the desired location.

The display 600 may also include a region/section 630 depicting the calcium arc angle. In this example, the extent to which calcium extends about the circumference of the blood vessel is represented. Here it can be seen that portions of the vessel may have calcium extending only a relatively short distance about the vessel and other portions of the vessel may have calcium extending about essentially the entire circumference of the blood vessel.

Figure 7:
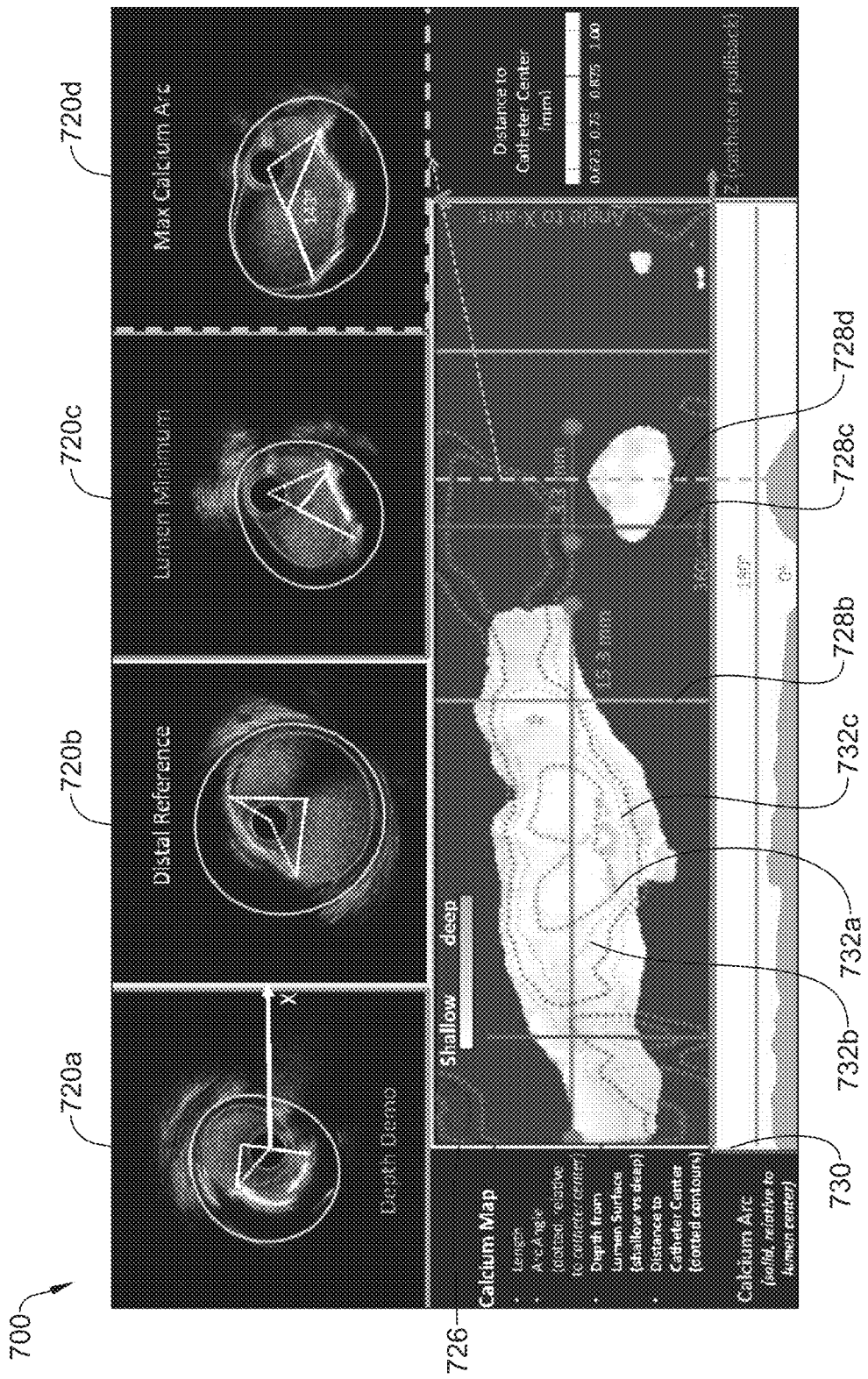
FIG. 7 illustrates a display for intravascular imaging data.

FIG. 7 illustrates a display 700 (e.g., where the display 700 refers to a visual/data component that may be displayed on a hardware component such as a display/display unit) that may be similar in form and function to other displays disclosed herein. The display 700 may include one or more transverse cross-sectional images of a blood vessel such as images 720a, 720b, 720c, 720d. In some instances, the cross-sectional images 720a, 720b, 720c, 720d (e.g., the data used to generate the images 720a, 720b, 720c, 720d) may be processed (e.g., using the processor 106) so that additional features may be marked thereon. For example, an indication of the lumen surface and/or an indication of the vessel surface may be marked on the images 720a, 720b, 720c, 720d. The images 720a, 720b, 720c, 720d may also be marked to indicate correspondence to a reference point (e.g., a distal reference point, a proximal reference point, etc.), a location corresponding to where the lumen area is at a minimum (e.g., the minimum lumen area), a location corresponding to where the calcium angle/arc is at a maximum, and/or other desired locations.

The display 700 may also include a calcium map 726. The calcium map 726 may include one or more reference markings/indicators such as reference markings 728b, 728c, 728d. As discussed with reference to FIG. 6, the reference markings 728b, 728c, 728d may be selectable and/or manipulatable by a user in order to customize the display 700 to include desired views.

The calcium map 726 may take the form of or otherwise resemble a topographic map with markings/indications that are representative of the distance that detected calcium/calcification is from the lumen surface and/or the markings/indications that are representative of the distance that detected calcium/calcification is from the catheter center. In some instances, the distance that detected calcium/calcification is from the lumen surface may be displayed using a color-coding system (where different colors or grayscale correspond to different depths). A visual scale may also be displayed to aid a user in determining the magnitude of the depths. In some instances, the distance that detected calcium/calcification is from the catheter center may use dashed contour lines. For example, contour lines 732a, 732b, 732c are shown in FIG. 7. Again, a visual scale may also be displayed to aid a user in determining the magnitude of the depths. Other features may also be shown in the calcium map 726. For example, the calcium map may include markings, colors, grays, etc. corresponding to calcium surface roughness/smoothness.

The display 700 may also include a region/section 730 depicting the calcium arc angle. In this example, the extent to which calcium extends about the circumference of the blood vessel is represented. Here it can be seen that portions of the vessel may have calcium extending only a relatively short distance about the vessel and other portions of the vessel may have calcium extending about essentially the entire circumference of the blood vessel.

It can be appreciated that the magnitude of the depths represented on the calcium map 726 may be relative to a center of an imaging catheter disposed in the vessel. Such a configuration/arrangement may be useful to a clinician to aid in ascertaining calcium/calcification of the vessel. In some of these and in other instances, the calcium map 726 may be capable of using and depicting calcium depths relative to the center of a guidewire positioned in the vessel. When doing so, the calcium map 726 and/or other components of the display 700 may be updated. In some instances, switching between a "catheter centered" and "guidewire centered" display 700 may include a user selecting the desired view, toggling a switch, and/or using another suitable user interface.

Figure 8:
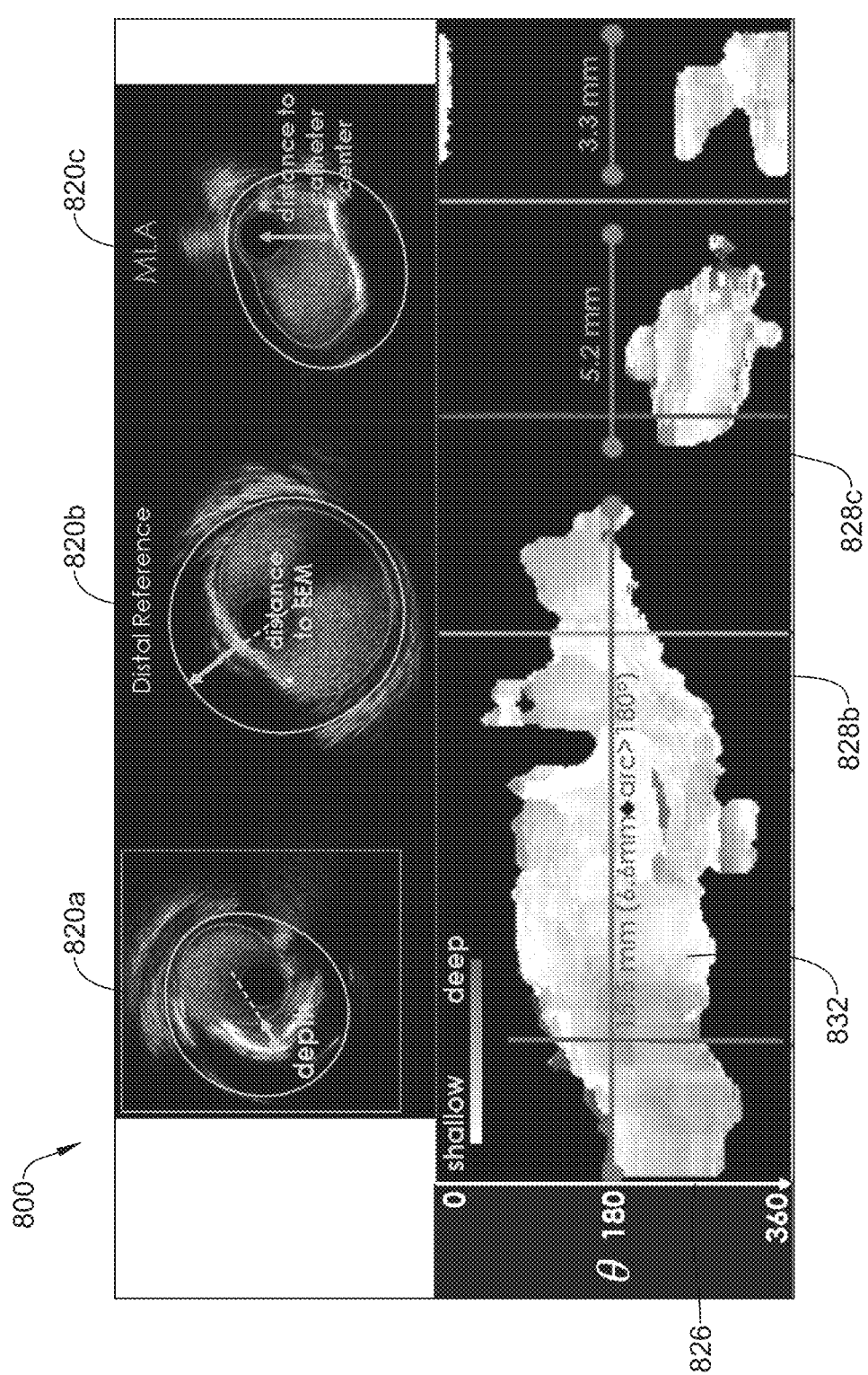
FIG. 8 illustrates a display for intravascular imaging data.

FIG. 8 illustrates a display 800 (e.g., where the display 800 refers to a visual/data component that may be displayed on a hardware component such as a display/display unit) that may be similar in form and function to other displays disclosed herein. The display 800 may include one or more transverse cross-sectional images of a blood vessel such as images 820a, 820b, 820c. In some instances, the cross-sectional images 820a, 820b, 820c (e.g., the data used to generate the images 820a, 820b, 820c) may be processed (e.g., using the processor 106) so that additional features may be marked thereon. For example, an indication of the lumen surface and/or an indication of the vessel surface may be marked on the images 820a, 820b, 820c. The images 820a, 820b, 820c may also be marked to indicate correspondence to a reference point (e.g., a distal reference point, a proximal reference point, etc.), a location corresponding to where the lumen area is at a minimum (e.g., the minimum lumen area), a location corresponding to where the calcium angle/arc is at a maximum, and/or other desired locations.

The display 800 may also include a calcium map 826. The calcium map 826 may include one or more reference markings/indicators such as reference markings 828b, 828c. As discussed with reference to FIG. 6, the reference markings 828b, 828c. may be selectable and/or manipulatable by a user in order to customize the display 800 to include desired views.

The calcium map 826 may take the form of or otherwise resemble a topographic map with markings/indications of calcium/calcification 832 that are representative of the distance that detected calcium/calcification is from the lumen surface. In some instances, the distance that detected calcium/calcification is from the lumen surface may be displayed using a color coding or grayscale system (where different colors/grays correspond to different depths). A visual scale may also be displayed to aid a user in determining the magnitude of the depths.

It can be appreciated that the magnitude of the depths represented on the calcium map 826 may be relative to a center of an imaging catheter disposed in the vessel. Such a configuration/arrangement may be useful to a clinician to aid in ascertaining calcium/calcification of the vessel. In some of these and in other instances, the calcium map 826 may be capable of using and depicting calcium depths relative to the center of a guidewire positioned in the vessel. When doing so, the calcium map 826 and/or other components of the display 800 may be updated. In some instances, switching between a "catheter centered" and "guidewire centered" display 800 may include a user selecting the desired view, toggling a switch, and/or using another suitable user interface.

Figure 9:
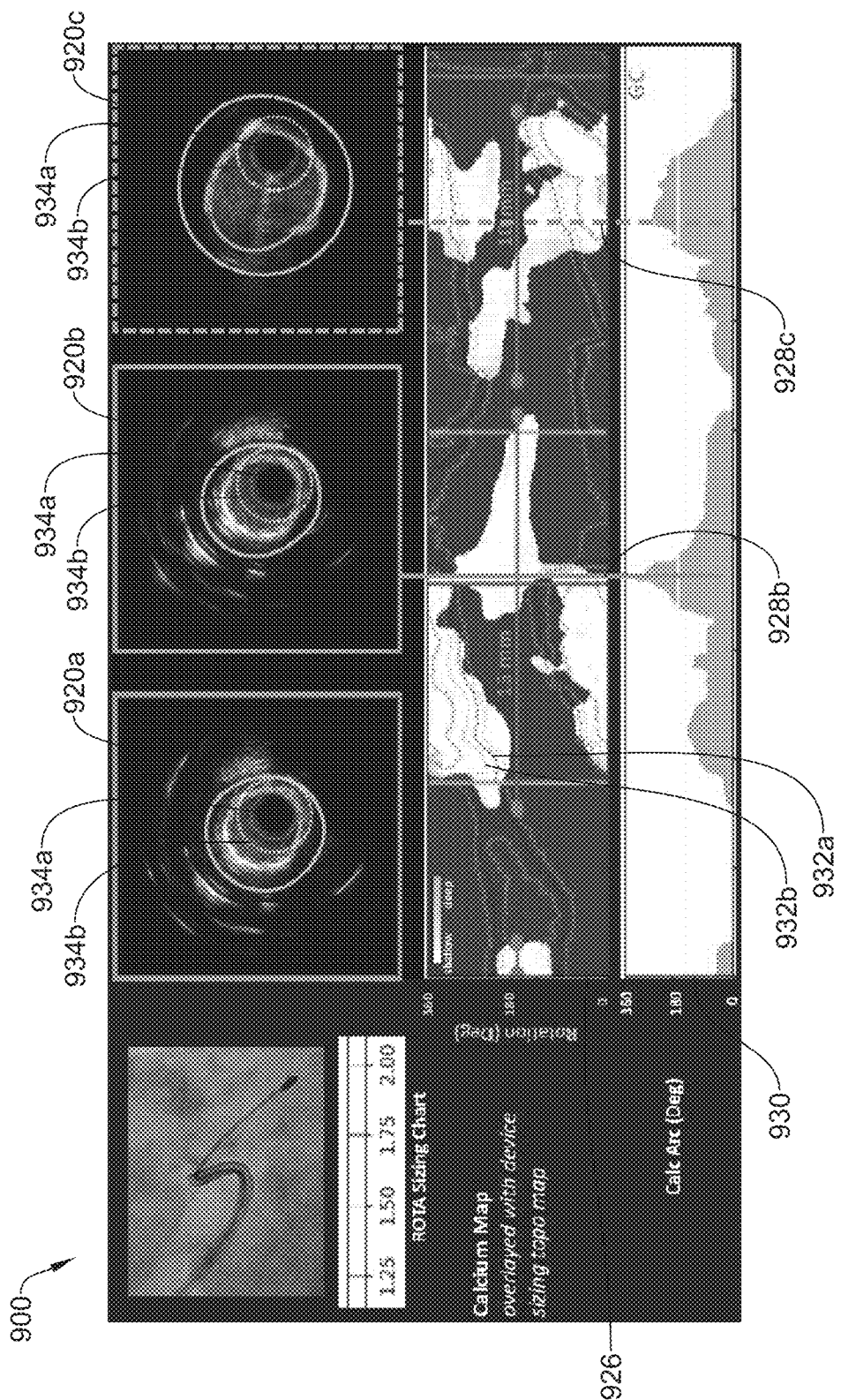
FIG. 9 illustrates a display for intravascular imaging data.

FIG. 9 illustrates a display 900 (e.g., where the display 900 refers to a visual/data component that may be displayed on a hardware component such as a display/display unit) that may be similar in form and function to other displays disclosed herein. The display 900 may include one or more transverse cross-sectional images of a blood vessel such as images 920a, 920b, 920c. In some instances, the cross-sectional images 920a, 920b, 920c (e.g., the data used to generate the images 920a, 920b, 920c) may be processed (e.g., using the processor 106) so that additional features may be marked thereon. For example, an indication of the lumen surface and/or an indication of the vessel surface may be marked on the images 920a, 920b, 920c. The images 920a, 920b, 920c may also be marked to indicate correspondence to a reference point (e.g., a distal reference point, a proximal reference point, etc.), a location corresponding to where the lumen area is at a minimum (e.g., the minimum lumen area), a location corresponding to where the calcium angle/arc is at a maximum, and/or other desired locations. In addition or in the alternative, the transverse cross-sectional images 920a, 920b, 920c may include one or more indicators of device reach such as indicators 934a, 934b, which may correspond to predicted rotational atherectomy depth. For example, rotational atherectomy devices are available in a variety of different sizes (e.g., different sized tips). By overlaying indicators 934a, 934b corresponding to differently sized rotational atherectomy tips, a clinician may be able to ascertain the extent to which a vessel stenosis may be impacted by differently sized rotational atherectomy tips.

It can be appreciated that the indicators 934a, 934b represented on the images 920a, 920b, 920c may be relative to a center of an imaging catheter disposed in the vessel. Such a configuration/arrangement may be useful to a clinician to aid in ascertaining a treatment strategy. In some of these and in other instances, the images 920a, 920b, 920c may be capable of using and depicting indicators 934a, 934b relative to the center of a guidewire positioned in the vessel. When doing so, the images 920a, 920b, 920c and/or other components of the display 900 may be updated. In some instances, switching between a "catheter centered" and "guidewire centered" display 900 may include a user selecting the desired view, toggling a switch, and/or using another suitable user interface.

The display 900 may also include a calcium map 926. The calcium map 926 may include one or more reference markings/indicators such as reference markings 928b, 928c. As discussed with reference to FIG. 6, the reference markings 928b, 928c may be selectable and/or manipulatable by a user in order to customize the display 900 to include desired views.

The calcium map 926 may take the form of or otherwise resemble a topographic map with markings/indications that are representative of the distance that detected calcium/calcification is from the lumen surface and/or the markings/indications that are representative of the distance that detected calcium/calcification is from the catheter center. In some instances, the distance that detected calcium/calcification is from the lumen surface may be displayed using a color-coding system (where different colors or grayscale correspond to different depths). A visual scale may also be displayed to aid a user in determining the magnitude of the depths. In some instances, the distance that detected calcium/calcification is from the catheter center may use dashed contour lines. For example, contour lines 932a, 932b are shown in FIG. 9. Again, a visual scale may also be displayed to aid a user in determining the magnitude of the depths. In some instances, the calcium map 926 may also include indicators corresponding to differently sized rotational atherectomy tips (e.g., similar to those in the images 920a, 920b, 920c, but altered to be compatible with the longitudinal view used for the calcium map 926).

The display 900 may also include a region/section 930 depicting the calcium arc angle. In this example, the extent to which calcium extends about the circumference of the blood vessel is represented. Here it can be seen that portions of the vessel may have calcium extending only a relatively short distance about the vessel and other portions of the vessel may have calcium extending about essentially the entire circumference of the blood vessel.

Figure 10:
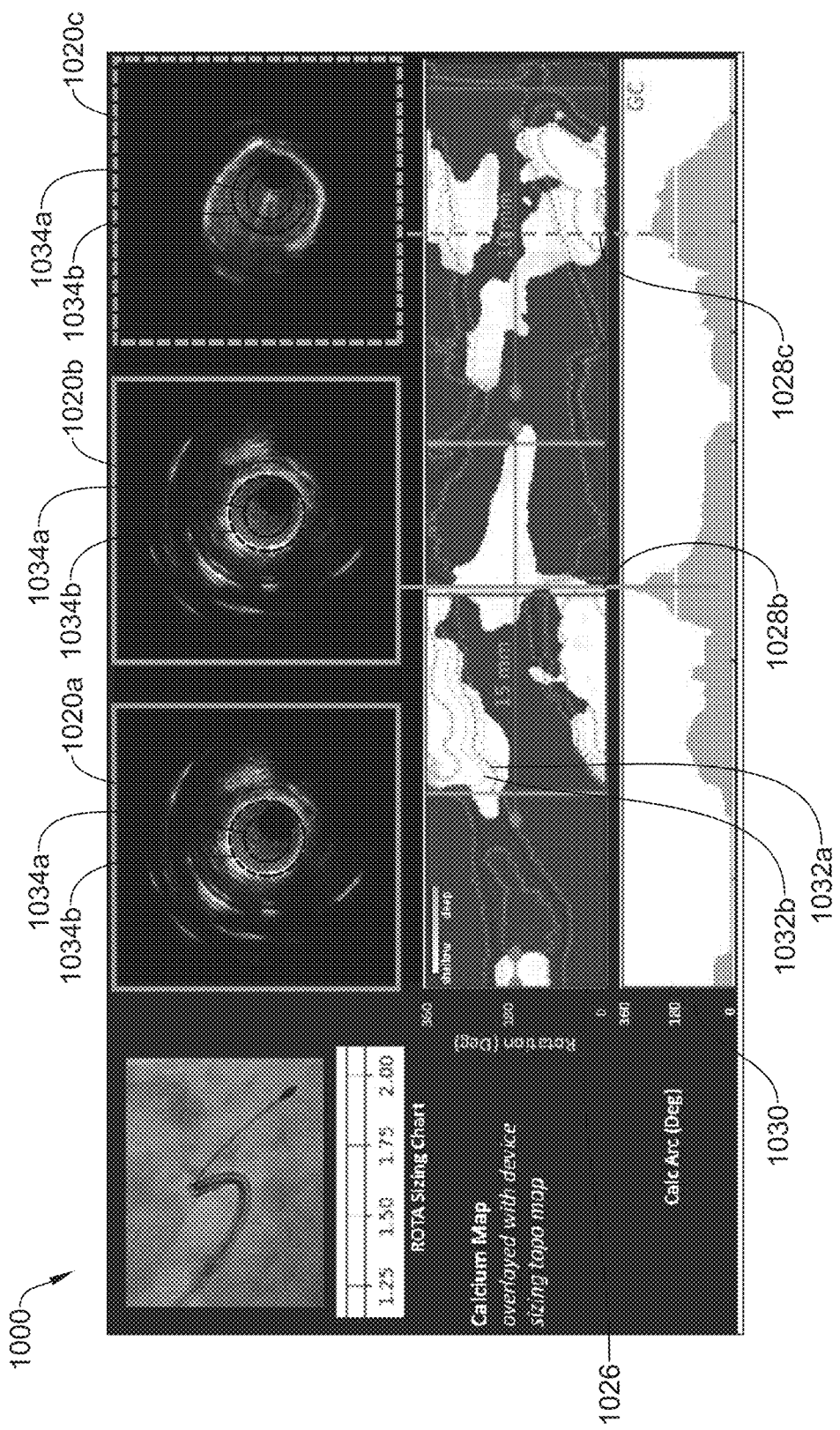
FIG. 10 illustrates a display for intravascular imaging data.

FIG. 10 illustrates a display 1000 (e.g., where the display 1000 refers to a visual/data component that may be displayed on a hardware component such as a display/display unit) that may be similar in form and function to other displays disclosed herein. The display 1000 may include one or more transverse cross-sectional images of a blood vessel such as images 1020a, 1020b, 1020c. In some instances, the cross-sectional images 1020a, 1020b, 1020c (e.g., the data used to generate the images 1020a, 1020b, 1020c) may be processed (e.g., using the processor 106) so that additional features may be marked thereon. For example, an indication of the lumen surface and/or an indication of the vessel surface may be marked on the images 1020a, 1020b, 1020c. The images 1020a, 1020b, 1020c may also be marked to indicate correspondence to a reference point (e.g., a distal reference point, a proximal reference point, etc.), a location corresponding to where the lumen area is at a minimum (e.g., the minimum lumen area), a location corresponding to where the calcium angle/arc is at a maximum, and/or other desired locations. In addition or in the alternative, the transverse cross-sectional images 1020a, 1020b, 1020c may include one or more indicators such as indicators 1034a, 1034b that correspond to predicted rotational atherectomy depth. For example, rotational atherectomy devices are available in a variety of different sizes (e.g., different sized tips). By overlaying indicators 1034a, 1034b corresponding to differently sized rotational atherectomy tips, a clinician may be able to ascertain the extent to which a vessel stenosis may be impacted by differently sized rotational atherectomy tips.

It can be appreciated that the indicators 934a, 934b represented on the images 920a, 920b, 920c shown in FIG. 9 may be relative to a center of an imaging catheter disposed in the vessel. In FIG. 10, the indicators 1034a, 1034b are depicted relative to the center of a guidewire positioned in the vessel. In some instances, switching between a "catheter centered" (e.g., as in FIG. 9) and the "guidewire centered" display 1000 may include a user selecting the desired view, toggling a switch, and/or using another suitable user interface.

The display 1000 may also include a calcium map 1026. The calcium map 1026 may include one or more reference markings/indicators such as reference markings 1028b, 1028c. As discussed with reference to FIG. 6, the reference markings 1028b, 1028c may be selectable and/or manipulatable by a user in order to customize the display 1000 to include desired views.

The calcium map 1026 may take the form of or otherwise resemble a topographic map with markings/indications that are representative of the distance that detected calcium/calcification is from the lumen surface and/or the markings/indications that are representative of the distance that detected calcium/calcification is from the catheter center. In some instances, the distance that detected calcium/calcification is from the lumen surface may be displayed using a color-coding system (where different colors or grayscale correspond to different depths). A visual scale may also be displayed to aid a user in determining the magnitude of the depths. In some instances, the distance that detected calcium/calcification is from the catheter center may use dashed contour lines. For example, contour lines 1032a, 1032b are shown in FIG. 10. Again, a visual scale may also be displayed to aid a user in determining the magnitude of the depths. In some instances, the calcium map 1026 may also include indicators corresponding to differently sized rotational atherectomy tips (e.g., similar to those in the images 1020a, 1020b, 1020c, but altered to be compatible with the longitudinal view used for the calcium map 1026).

The display 1000 may also include a region/section 1030 depicting the calcium arc angle. In this example, the extent to which calcium extends about the circumference of the blood vessel is represented. Here it can be seen that portions of the vessel may have calcium extending only a relatively short distance about the vessel and other portions of the vessel may have calcium extending about essentially the entire circumference of the blood vessel.

Figure 11:
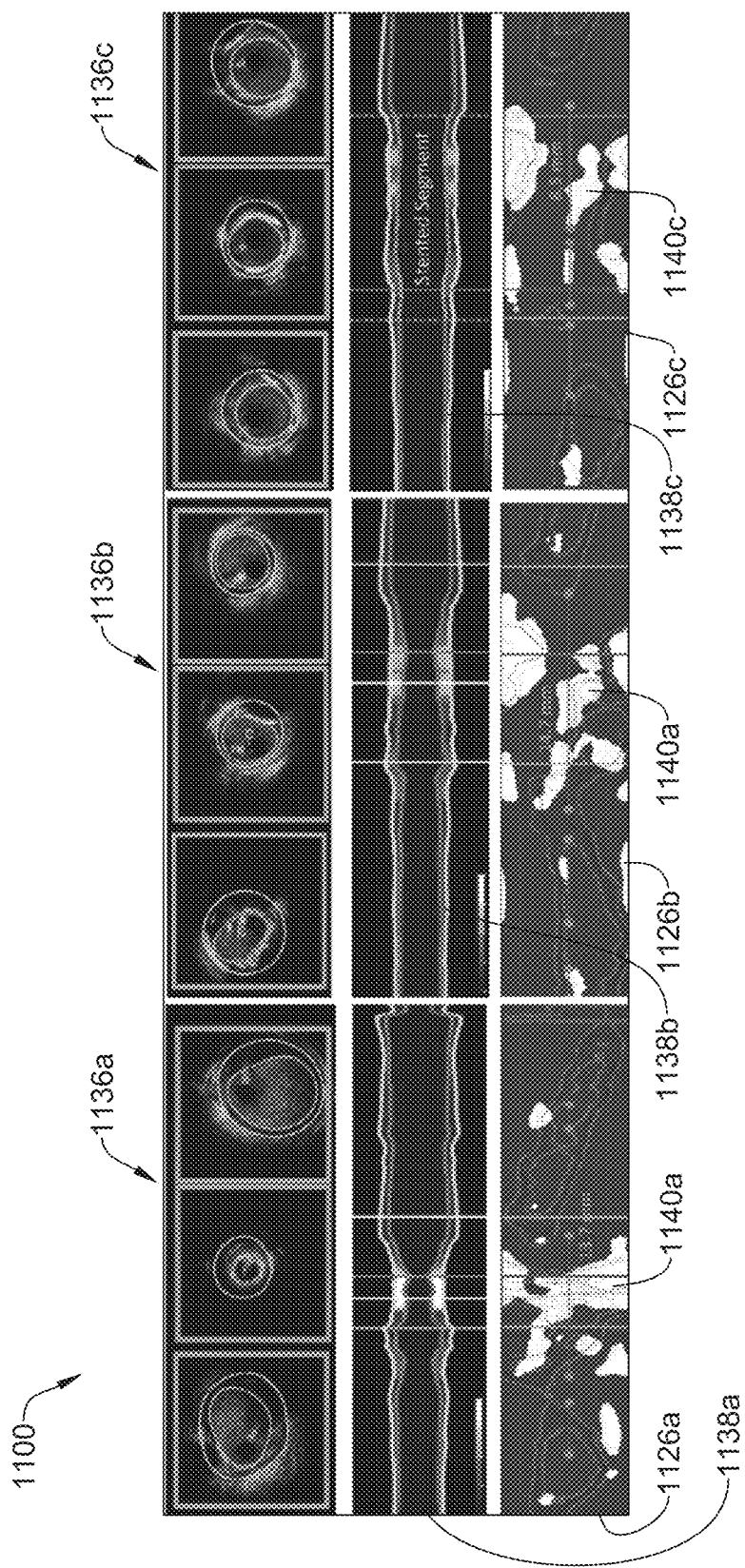
FIG. 11 illustrates a display for intravascular imaging data.

FIG. 11 illustrates a display 1100 (e.g., where the display 1100 refers to a visual/data component that may be displayed on a hardware component such as a display/display unit) that may be similar in form and function to other displays disclosed herein. The display 1100 may include three panels 1136a, 1136b, 1136c. Each of the panels may represent a different time period of an intervention. For example, panel 1136a may include cross-sectional images of a blood vessel, a longitudinal vessel profile 1138a with calcium markings/indications, and a calcium map 1126a for a time period prior to an intervention. Panel 1136b may include cross-sectional images of a blood vessel, a longitudinal vessel profile 1138b with calcium markings/indications, and a calcium map 1126b for a time period after a vessel preparation procedure. Panel 1136c may include cross-sectional images of a blood vessel, a longitudinal vessel profile 1138c with calcium markings/indications, and a calcium map 1126c for a time period after a treatment.

The calcium maps 1126a, 1126b, 1126c may include sections 1140a, 1140b, 1140c of calcium. Changes in the calcium sections 1140a, 1140b, 1140c may show changes over the course of a procedure. For example, the calcium section 1140a in panel 1136a may extend fully circumferentially about the blood vessel prior to treatment. The vessel may be prepped, for example by treating an interventional device such as an angioplasty balloon, a cutting balloon, and/or the like. The calcium section 1140b can be seen as broken up in panel 1136b after the preparation process. Following treatment, the calcium section 1140c can be seen as further broken up and separated in panel 1136c.

Figure 12:
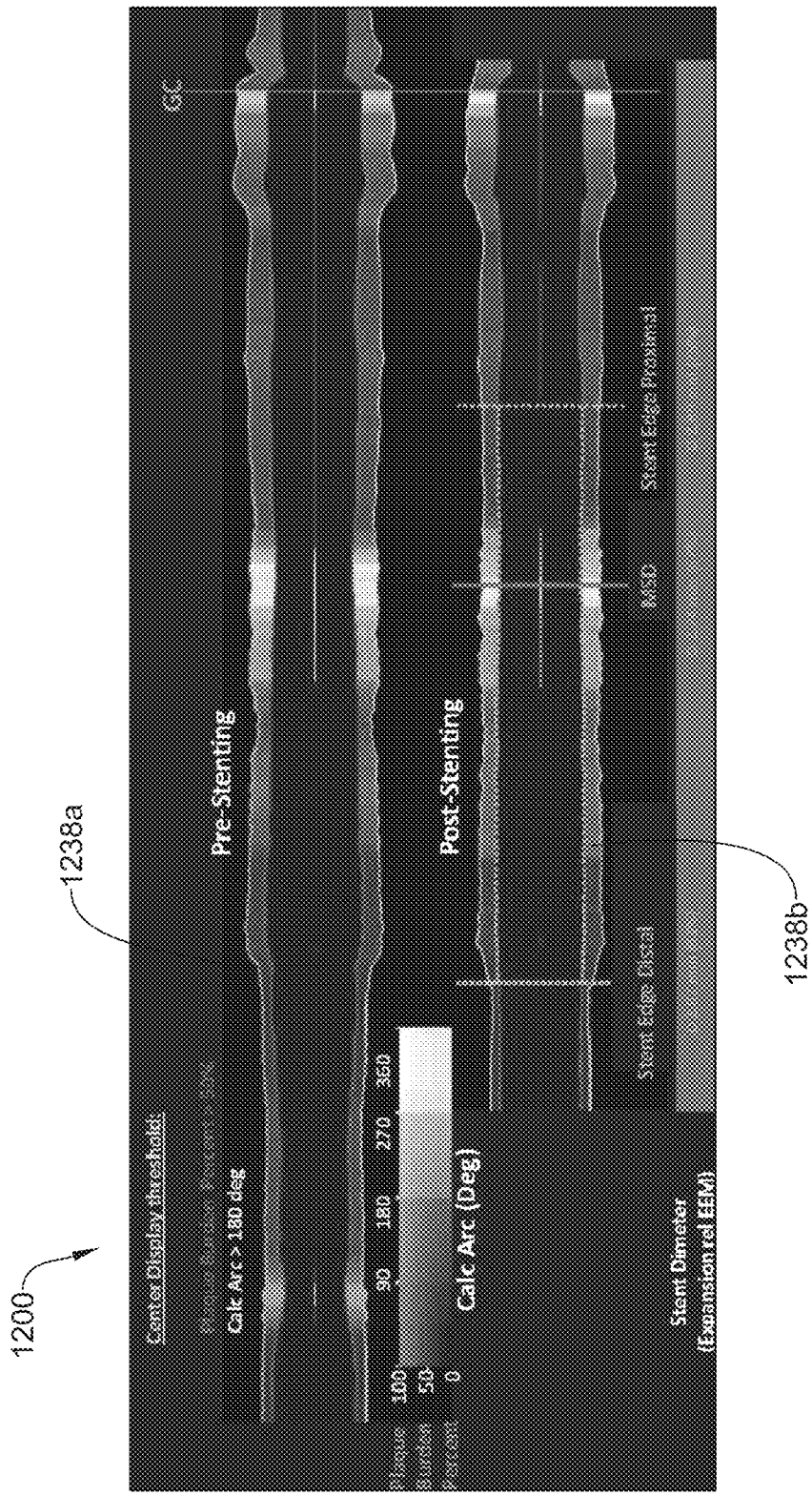
FIG. 12 illustrates a display for intravascular imaging data.

FIG. 12 illustrates a display 1200 (e.g., where the display 1200 refers to a visual/data component that may be displayed on a hardware component such as a display/display unit) that may be similar in form and function to other displays disclosed herein. The display may include a first longitudinal view 1238a and a second longitudinal view 1238b. The first longitudinal view 1238a may represent the blood vessel prior to treatment. The vessel wall may include color/grayscale colorings corresponding to calcium arc/angle. In this example, a brightened spot may correspond to a location where the calcium arc/angle approaches 360 degrees. The second longitudinal view 1238b may represent the blood vessel after a treatment (e.g., after deploying a stent in the vessel). The vessel wall may include color/grayscale colorings corresponding to calcium arc/angle. In this example, a previously-seen bright spot from the first longitudinal view 1238a may be less bright, indicating that the calcium may be partially broken up and less circumferential about the vessel.

Figure 13:
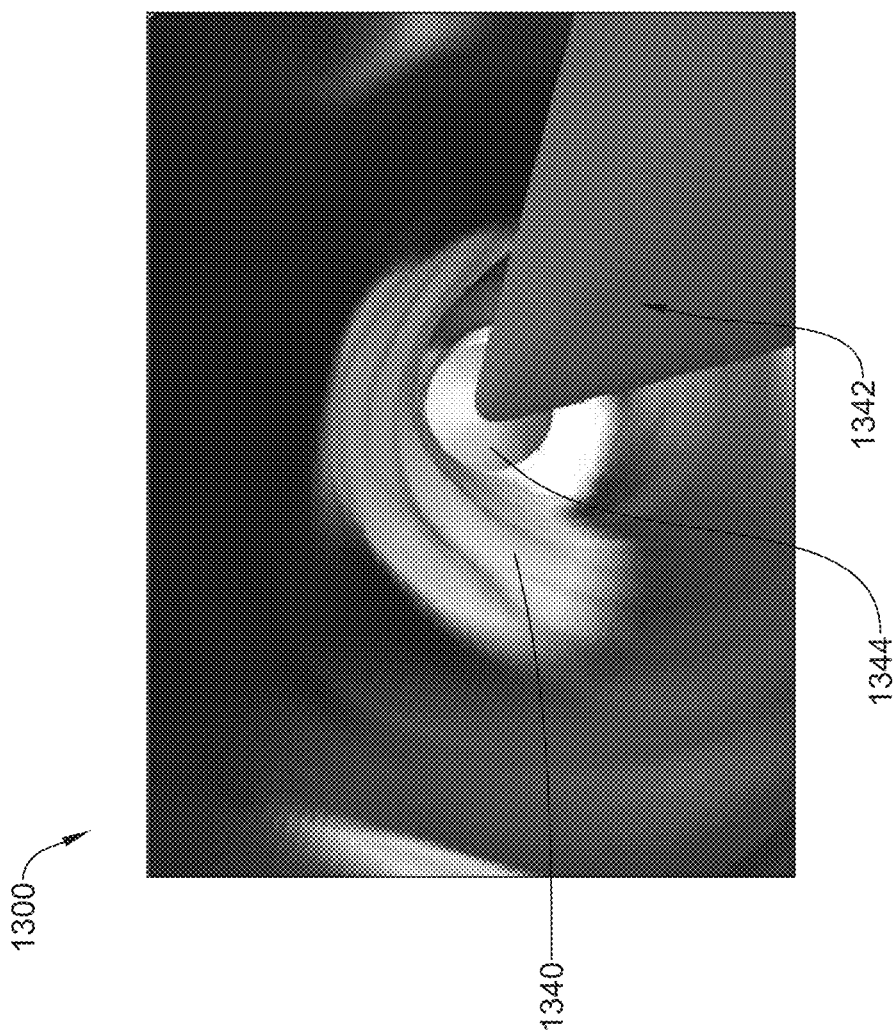
FIG. 13 illustrates a display for intravascular imaging data.
Figure 14:
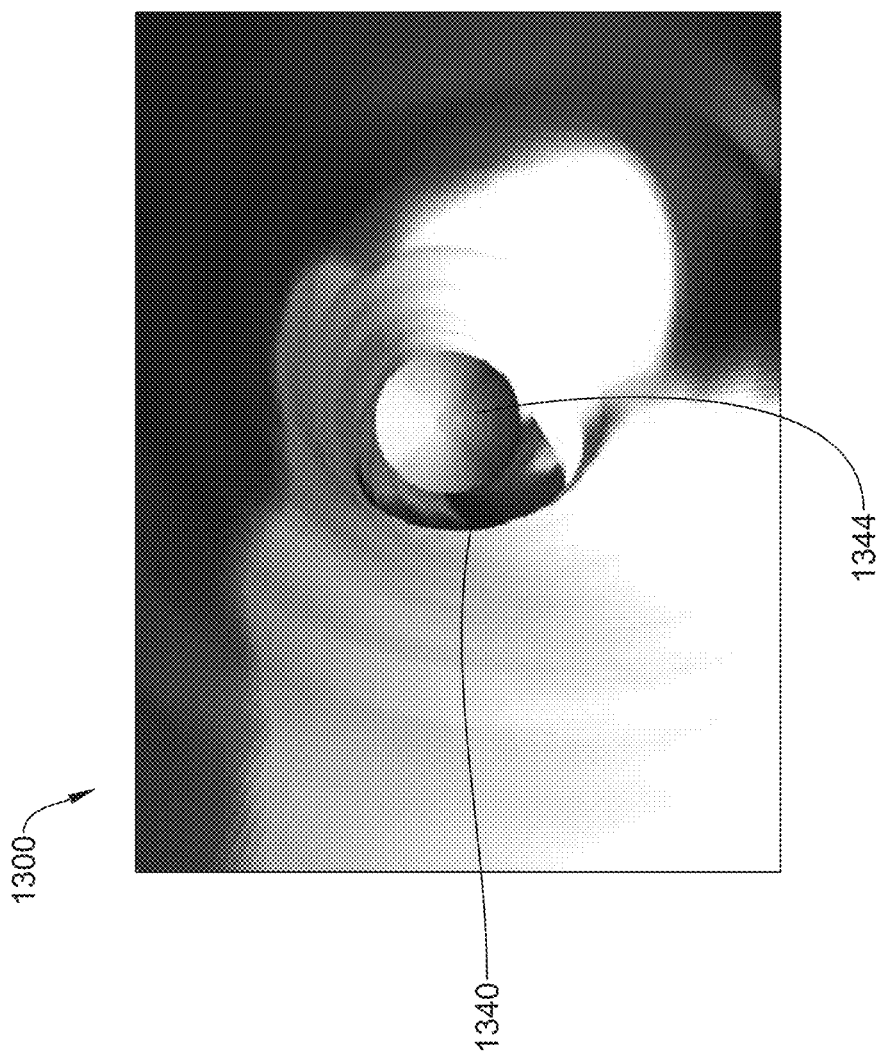
FIG. 14 illustrates a display for intravascular imaging data.

FIGS. 13-14 illustrate a display 1300 (e.g., where the display 1300 refers to a visual/data component that may be displayed on a hardware component such as a display/display unit) that may be similar in form and function to other displays disclosed herein. The display may include images or a video representation of a "virtual fly through" of the vessel. For example, the display 1300 may show the vessel 1340 and a treatment catheter 1342 including a treatment device 1344 coupled thereto. In some instances, the display may be arranged as a video where the catheter 1342 is depicted in a way that appears as though it is moving through the vessel. In FIG. 13, the view is looking in the distal direction whereas in FIG. 14 the view is flipped in orientation. In some instances, the virtual fly through depiction may include a view showing predicted thrombus removed using the catheter 1342. In other words, the virtual fly through may predict the result of treating the vessel with the catheter 1342. The image(s)/video can be obtained through a 3-dimensional lumen surface of volume rendering.

Some example IVUS imaging systems that may be used, for example with the methods disclosed herein, include, but are not limited to, those disclosed in, for example, U.S. Pat. Nos. 7,246,959; 7,306,561; and 6,945,938; as well as U.S. Patent Application Publication Nos. US 2006/0100522; US 2006/0106320; US 2006/0173350; US 2006/0253028; US 2007/0016054; and US 2007/0038111; all of which are incorporated herein by reference.

U.S. Patent Application Publication No. US 2015/0073279 is herein incorporated by reference.

U.S. Patent Application No. 62/906,546 is herein incorporated by reference.

WO 2021/062006 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular imaging system, comprising:
a catheter including an imaging device;
a processor coupled to the catheter, the processor configured to process image data received from the imaging device;
wherein the processor is configured to generate a calcium map;
wherein the calcium map includes an indicator of calcium depth to a vessel lumen surface, calcium distance to a center of the catheter, or both;
wherein the calcium map includes a longitudinal cross-sectional view with a topographic depiction of calcium depth to the vessel lumen surface, a topographic depiction of calcium distance to the center of the catheter, or both; and
a display unit coupled to the processor, the display unit being configured to show a display including the calcium map.

2. The intravascular imaging system of claim 1, wherein the calcium map includes a grayscale depiction of calcium depth to the vessel lumen surface.

3. The intravascular imaging system of claim 1, wherein the calcium map includes a grayscale depiction of calcium distance to the center of the catheter.

4. The intravascular imaging system of claim 1, wherein the display includes a transverse cross-sectional depiction of a blood vessel.

5. The intravascular imaging system of claim 4, wherein the transverse cross-sectional depiction of the blood vessel includes one or more treatment device representations overlaid thereon.

6. The intravascular imaging system of claim 5, wherein the one or more treatment device representations includes one or more depictions of a rotational atherectomy device size.

7. The intravascular imaging system of claim 1, wherein the display includes a plurality of panels corresponding to different time periods during an intervention.

8. The intravascular imaging system of claim 7, wherein the plurality of panels includes a pre-treatment panel, a lesion prep panel, and a post-treatment panel.

9. The intravascular imaging system of claim 1, wherein the imaging device includes an intravascular ultrasound device.

10. The intravascular imaging system of claim 1, wherein the imaging device includes an optical coherence tomography device.

11. An intravascular imaging system, comprising:
- a catheter system including an intravascular imaging device;
- a processor coupled to the catheter system, the processor configured to process image data received from the intravascular imaging device;
- wherein the processor is configured to generate a calcium map that graphically depicts an indicator of calcium depth to a vessel lumen surface, calcium distance to a center of the catheter system, or both;
- wherein the calcium map includes a longitudinal cross-sectional view with a topographic depiction of calcium depth to the vessel lumen surface, a topographic depiction of calcium distance to the center of the catheter, or both; and
- a display unit coupled to the processor, the display unit being configured to show a display including the calcium map.

12. The intravascular imaging system of claim 11, wherein the display includes a transverse cross-sectional depiction of a blood vessel.

13. The intravascular imaging system of claim 12, wherein the transverse cross-sectional depiction of the blood vessel includes one or more treatment device representations overlaid thereon.

14. The intravascular imaging system of claim 13, wherein the one or more treatment device representations includes one or more depictions of a rotational atherectomy device size.

15. The intravascular imaging system of claim 11, wherein the display includes a plurality of panels corresponding to different time periods during an intervention including a pre-treatment panel, a lesion prep panel, and a post-treatment panel.

16. An intravascular imaging system, comprising:
- a catheter system including an intravascular ultrasound imaging device;
- a processor computed to the catheter system, the processor configured to process image data received from the intravascular ultrasound imaging device;
- wherein the processor is configured to use artificial intelligence to generate a calcium map that graphically depicts an indicator of calcium depth to a vessel lumen surface, calcium distance to a center of the catheter system, or both;
- wherein the calcium map includes a longitudinal cross-sectional view with a topographic depiction of calcium depth to the vessel lumen surface, a topographic depiction of calcium distance to the center of the catheter, or both; and
- a display unit coupled to the processor, the display unit being configured to show a display including the calcium map.

* * * * *